United States Patent
Bousse et al.

(10) Patent No.: US 8,394,324 B2
(45) Date of Patent: Mar. 12, 2013

(54) MICROCHIP LARGE-VOLUME PCR WITH INTEGRATED REAL-TIME CE DETECTION

(75) Inventors: Luc Bousse, Los Altos, CA (US); Jian-ping Zhang, Moraga, CA (US)

(73) Assignee: Wako Pure Chemical Industries, Ltd., Osaka (JP)

( * ) Notice: Subject to any disclaimer, the term of this patent is extended or adjusted under 35 U.S.C. 154(b) by 561 days.

(21) Appl. No.: 12/664,018

(22) PCT Filed: Jun. 11, 2008

(86) PCT No.: PCT/US2008/007359
§ 371 (c)(1),
(2), (4) Date: Dec. 10, 2009

(87) PCT Pub. No.: WO2008/154036
PCT Pub. Date: Dec. 18, 2008

(65) Prior Publication Data
US 2010/0173310 A1    Jul. 8, 2010

Related U.S. Application Data

(60) Provisional application No. 60/943,248, filed on Jun. 11, 2007.

(51) Int. Cl.
| | |
|---|---|
| G01N 15/06 | (2006.01) |
| G01N 33/00 | (2006.01) |
| G01N 33/48 | (2006.01) |
| C12Q 1/68 | (2006.01) |
| C12P 19/34 | (2006.01) |
| C12M 1/36 | (2006.01) |
| C12M 1/38 | (2006.01) |
| C12M 3/00 | (2006.01) |
| C12M 1/34 | (2006.01) |

(52) U.S. Cl. ...... 422/68.1; 435/6.1; 435/91.1; 435/91.2; 435/288.5

(58) Field of Classification Search .................. 422/68.1
See application file for complete search history.

(56) References Cited

U.S. PATENT DOCUMENTS

| 5,691,141 | A | 11/1997 | Köster |
| 5,872,010 | A | 2/1999 | Karger et al. |
| 6,803,568 | B2 | 10/2004 | Bousse et al. |
| 7,105,812 | B2 | 9/2006 | Zhao et al. |
| 7,228,237 | B2 | 6/2007 | Woo et al. |
| 2003/0148922 | A1 | 8/2003 | Knapp et al. |
| 2005/0129582 | A1 | 6/2005 | Breidford et al. |
| 2007/0017812 | A1 | 1/2007 | Bousse |
| 2007/0111303 | A1 | 5/2007 | Inoue et al. |
| 2007/0119711 | A1 | 5/2007 | Ausserer et al. |

FOREIGN PATENT DOCUMENTS
WO  PCT/US2008/006266    11/2008

OTHER PUBLICATIONS

Kim, 2005, Anal. Chem., 77:6494-6499.*
International Search Report from the U.S. Patent and Trademark Office for International Application No. PCT/US2008/007359 (Aug. 20, 2008).

* cited by examiner

*Primary Examiner* — Valarie Bertoglio
(74) *Attorney, Agent, or Firm* — Finnegan, Henderson, Farabow, Garrett & Dunner, LLP

(57) ABSTRACT

A microfluidic device is provided with appropriate integrated structures to conduct large volume PCR and end-point or real-time capillary electrophoresis detection. The microfluidic device includes a substrate having an amplification chamber of a volume of nucleic acid, wells disposed on the substrate, flow channels connecting the wells and the chamber in the substrate to allow for solution flow through the chamber, and one or more separation channels provided in the substrate and connected to the chamber for separating and detecting a fraction of the amplified nucleic acid. The chamber, the flow channels, and the one or more separation channels are configured such that the hydrodynamic flow resistance of the chambers and the flow channels combined is at least 10^3 times smaller than the hydrodynamic flow resistance in the one or more separation channels. The microfluidic device can achieve a very high sensitivity in detection while being highly cost effective.

23 Claims, 9 Drawing Sheets

MICROCHIP LARGE-VOLUME PCR WITH INTEGRATED REAL-TIME CE DETECTION

PRIORITY INFORMATION

This application is the national stage of International Application No. PCT/US2008/007359, filed Jun. 11, 2008, which claims the benefit of U.S. Provisional Application No. 60/943,248, filed Jun. 11, 2007, which is incorporated herein by reference.

FIELD OF THE INVENTION

The invention relates to a microfluidic device for carrying out large volume polymerase chain reaction (PCR) and integrated capillary electrophoresis (CE) detection.

BACKGROUND OF THE INVENTION

Microfluidic PCR is generally defined as PCR in chambers with the dimensions being very small, for example between a range of 500 and 0.5 μm. There are microfluidic systems with various heating systems such as zone heating, external heaters, integrated resistors, Joule heating, and infrared radiation, but those systems require external detection. That means that at the end of the reaction, some of the sample has to be physically removed from the PCR chamber and analyzed externally from the system by means such as gel electrophoresis or capillary electrophoresis. Examples of work of this type are described in Cheng et al. Nucleic Acids Res, 24(2), p. 380-5 (1996); Kopp and Manz, Science, 280(5366) p. 1046-8 (1998); Oda Anal Chem, 70(20), p. 4361-8 (1998); and Chen et al. Anal Chem, 77(2): p. 658-66 (2005). A system requiring external detection would be incompatible with real-time detection functions because such a system would require removal of a large part of the PCR reaction solution for external measurements.

Another detection method uses optical detection, which involves intercalating dyes such as SYBR Green (see Rasmussen et al., Biochemica, 1998(2): p. 8-111998), or fluorogenic probes such as Taqman probes (see Kalinina, O., et al., Nucleic Acids Res, 25(10), p. 1999-2004 (1997); Belgrader, P., et al., Science, 284(5413), p. 449-50 (1999); Belgrader, P., et al. Anal Chem, 75(14), p. 3446-50 (2003); and Northrup, M. A., et al., Anal Chem, 70(5), p. 918-22 (1998)). SYBR Green dye is a highly specific, double-stranded DNA binding dye for detecting DNA product as it accumulates during PCR cycles. Although both detection methods can be used in a real-time PCR amplification, a distinction between the intercalating dye and the Taqman probe techniques is that the intercalating dye detection method is not specific. It will detect all double-stranded DNA, including non-specific PCR products such as primer-dimer formations. For this reason PCR amplification with an intercalating dye often requires a melting curve analysis to distinguish between a desired PCR product and non-specific PCR amplification.

In contrast, the Taqman probe PCR detection method is highly specific because the generation of fluorescent signal depends on the specific hybridization between the probe and the desired PCR product. However, the Taqman probe PCR detection method requires, unlike SYBR Green dye, synthesizing individual probes for different sequences, is constrained by the limitation of fluorescent dyes that can be used for probe labeling (limited by the number of different color dyes, for example), and needs expensive reagents.

An alternative detection method for PCR is to perform an electrophoretic DNA size separation of the reaction products. This allows the desired reaction product to be identified separately from all other sources of DNA or contaminants. Many microfluidic PCR systems with external detection involve DNA sizing, either on a gel or by capillary electrophoresis, because it is specific and does not require target-specific probe synthesis.

SUMMARY OF THE INVENTION

A microfluidic system for nucleic acid amplification and detection is provided. The system includes a substrate having a chamber for amplification of a volume of nucleic acid; wells disposed on the substrate; flow channels connecting the wells and the chamber in the substrate to allow for flow of solution through the chamber; and one or more separation channels provided in the substrate and connected to the chamber for separating and detecting a fraction of the amplified nucleic acid in the chamber. The chamber, the flow channels, and the one or more separation channels are configured such that the hydrodynamic flow resistance of the chambers and the flow channels combined is about $10^3$ or more smaller, or about $10^3$ times to about $10^9$ times smaller, or about $10^3$ to about $10^7$ smaller, or about $10^4$ to about $10^6$ smaller than the hydrodynamic flow resistance in the one or more separation channels. The term hydrodynamic flow resistance or hydraulic flow resistance denotes resistance to pressure-driven flow and can be defined as the ratio of pressure difference divided by flow rate. The system may further include a thermal cycling device or other members to carry out the separation.

Further, a microfluidic system for nucleic acid amplification and detection is provided that includes a substrate providing a chamber for amplification of a volume of nucleic acid; wells disposed on the substrate; flow channels connecting the wells and the chamber in the substrate to allow for flow of solution through the chamber; and one or more separation channels provided in the substrate and connected to the chamber for separating and detecting a fraction of the amplified nucleic acid in the chamber, where the combined volume of the one or more separation channels is more than 100 times or more smaller or from about 100 times to about 1000 times smaller, or from about 300 times to about 1000 times smaller than the combined volume of the chamber and the flow channels.

The system may further include a thermal cycling device or an optical-reading control device to carry out the separation and to quantify the DNA.

Further still, a microfluidic device for nucleic acid amplification and detection is provided that includes a substrate providing a chamber for amplification of a volume of nucleic acid; wells provided in the substrate; flow channels connecting the wells and the chamber in the substrate to allow for flow of solution through the chamber; and one or more separation channels provided in the substrate and connected to the chamber for separating and detecting a fraction of the amplified nucleic acid in the chamber, where the dimension of the one or more separation channels is smaller than the dimension of each of the flow channels and the chamber such that the hydrodynamic flow resistance in the one or more separation channels serve in place of a valve.

Moreover, a method for nucleic acid amplification and detection is provided that includes (1) providing a microfluidic device containing a chamber for amplifying a volume of nucleic acid, wells, and flow channels connected to the wells and the chamber to allow for flow of solution through the chamber, and one or more separation channels connected to the chamber; (2) disposing a nucleic acid solution in the chamber; (3) amplifying the nucleic acid disposed in the chamber; (4) introducing a fraction of the amplified nucleic acid from the chamber into the one or more separation channels; (5) separating the fraction of the amplified nucleic acid through the one or more separation channels; and (6) detecting the separated nucleic acid. Steps (3) to (6) are repeated one or more times for real time detection, or step (3) is repeated one or more times and then steps (4) to (6) are executed for end-point detection. The method may further include (8) quantifying the amount of nucleic acid present based on data collected.

Therefore, the device and the method are suitable for real-time as well as end-point PCR assays.

The nucleic acid separation can be carried out using electrokinetic methods. The term electrokinetic is generally understood to mean the movement of solutions or molecules in response to an electric field. It includes electrophoresis, which is the movement of ions or charged molecules in an electric field, and electroosmosis, which is the movement of bulk solution due to an electric field. Nucleic acid separations can be carried out in conditions where electrophoresis dominates, and the nucleic acids have size-dependent mobilities due to the presence of a sieving matrix. However, other methods of separating nucleic acids exist, and could be used in a microfluidic system or device. For example, DNA has been sequenced by separating DNA fragments by mass spectrometry (U.S. Pat. No. 5,691,141; Koster et al., Nature Biotech. Vol. 14, p. 1123 (1996)), and many microfluidic to mass spectrometry interfaces have been described (see for example U.S. Pat. Nos. 5,872,010, 6,803,568, and 7,105,812). Another method of separating nucleic acids relies on hybridization to immobilized probes, as described for instance by Lenigk et al. (Anal. Biochem. Vol. 311, p. 40 (2002)). The term "separating" or "separation" is used in a general sense unless further restricted.

Additional features of the invention will be set forth in part in the description which follows, and in part will be understood from the description, or may be learned by practice of the invention. The features of the invention may be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention. Furthermore, all of the references mentioned in this specification are incorporated herein by reference.

DESCRIPTION OF THE EMBODIMENTS

Figure 1A:
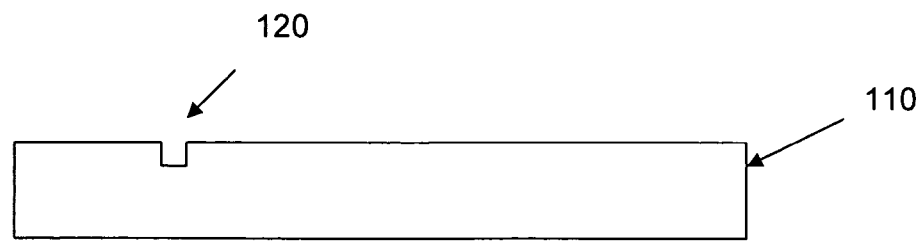
FIGS. 1(A)-(E) is an illustrative example of a manufacturing method of a microfluidic chip with PCR-CE capabilities on a single substrate.
Figure 1B:
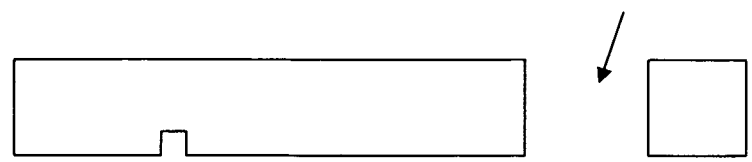
Figure 1C:
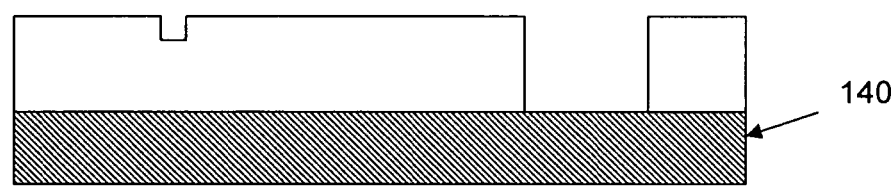
Figure 1D:
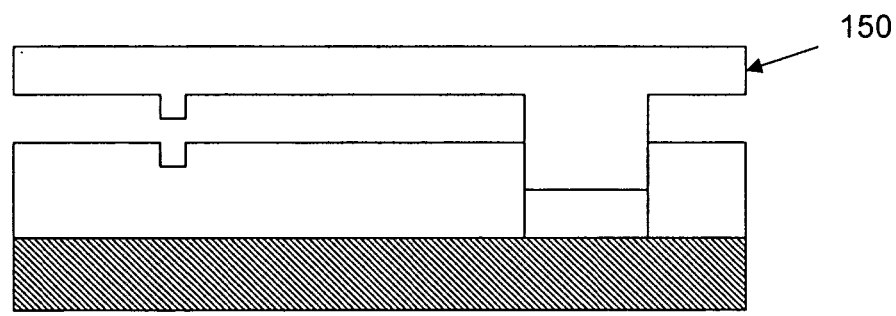
Figure 1E:
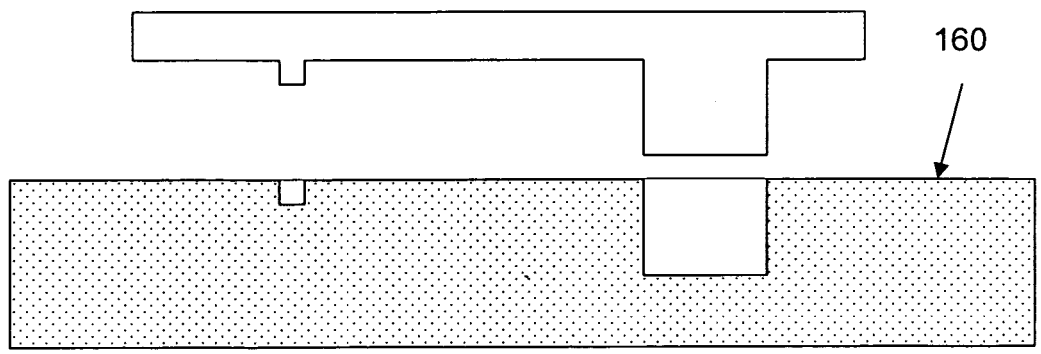

Reference will now be made in detail to the present embodiments (exemplary embodiments) of the invention, examples of which are illustrated in the accompanying drawings. Wherever possible, the same reference numbers will be used throughout the drawings to refer to the same or like parts.

An embodiment of the present invention, a microfluidic system can be configured to have the following features: A PCR chamber can have a volume from about 1 µl to about 100 µl, about 10 µl to about 75 µl, or about 25 µl to about 50 µl to provide high sensitivity for DNA amplification. As an example, if the lowest copy number that can reliably be amplified is 10, then in a 10 µl volume the limit to sensitivity is one copy per µl. In a 100 nl volume, the limiting sensitivity would be 100 copies per µl, which is 100 times lower. Another feature is that the system is equipped for thermal cycling the contents of the PCR chamber to achieve sufficient DNA amplification. Still another feature is that the system has a network of channels of sufficiently small dimensions connected to the PCR chamber. The network of channels, called the separation channels, can be configured to have a smaller internal volume than the PCR chamber in order to facilitate the analysis of a very small fraction of the nucleic acid contained in the chamber. The combined volume of the separation channels can be about 100 times or more smaller or from about 100 times to about 1000 times smaller, or from about 300 to about 1000 times smaller than that of the PCR chamber and the flow channels. Also, the dimensions of the channels are kept small to ensure the hydrodynamic flow resistance of these channels is much higher than the PCR chamber and other channels leading to the chamber. By making that ratio of flow resistances very high in the range of about $10^3$ or more, or about $10^3$ to about $10^9$, or about $10^3$ to about $10^7$, or about $10^4$ to about $10^6$, a gate function without any valves or plugs can be achieved at the channels. In another feature, the network of channels can be used for an electrophoretic DNA sizing assay. To implement this sizing assay, a simple cross channel topology can be employed to fill the channels with a DNA sieving matrix. Still another feature is that fabrication of the entire system is made in a single, disposable, substrate.

Avoiding the use of valves or plugs has merits. Microfluidic valves exist, but require a more complex fabrication sequence than the system described here, with several more layers, and alignment requirements. That makes systems with valves typically expensive to fabricate as disposable devices. Furthermore, microfluidic valves may suffer from dead volume and leakage flows. The use of plugs, or gel valves, such as described by Koh et al. (Anal. Chem., Vol. 75, p. 4591 (2003)) may not be cost-effective and shelf-life may be limited. Moreover, nucleic acid transport through a cross-linked gel plug is relatively slow, and will cause the analysis to take longer. As a result, it may only be practical to perform an end-point analysis, rather than a real-time PCR quantification.

By using mainly electrophoretic forces to transport nucleic acids, a very small fraction of the nucleic acid in the PCR chamber can be removed for analysis, without removing a similar fraction of the solution in the chamber. Removing even a small aliquot of solution such as 10 µl, as described for instance by Slepnev (U.S. Pat. No. 7,081,339), may result in losing a significant fraction of the nucleic acid in the PCR chamber, and therefore, may make real-time analysis difficult.

A large PCR chamber in a microfluidic chip may be combined with small capillary electrophoresis (CE) separation channels such that the hydrodynamic flow resistance of the separation channels is sufficiently greater than that of the large PCR chamber. A ratio of the resistance in the separation channels to that of the PCR chamber required to achieve high quality separations can be calculated. For an exemplary calculation to arrive at an estimated range of the resistance ratio for designing a PCR-CE chip, a pressure difference, $\Delta P$, is assumed to drive a solution in or out of the PCR chamber and along the separation channel. The pressure difference $\Delta P$ can be described as follows:

$$\Delta P = R_{chamber} V_{chamber}$$

where $R_{chamber}$ is the hydrodynamic resistance to flow of the PCR chamber and $V_{chamber}$ is the volume of the PCR chamber. To make the calculation simple, the hydrodynamic resistance of the chamber is approximated to include the resistance of flow channels, which are non-CE separation channels; thus whenever the resistance of the chamber is mentioned below, the resistance of the flow channels is assumed to be included. A flow rate can be expressed in terms of the fraction of the chamber volume that is lost, divided by the time of the analysis:

$$Q_{chamber} = \frac{fV_{chamber}}{t_{anal}}$$

where $Q_{chamber}$ is the flow rate through this chamber, and f is the fraction of this volume that is lost. In terms of these variables, the hydrodynamic flow resistance $R_{chamber}$ can be given by:

$$R_{chamber} = \frac{\Delta P}{Q_{chamber}} = \frac{\Delta P t_{anal}}{fV_{chamber}}$$

Figure 2:
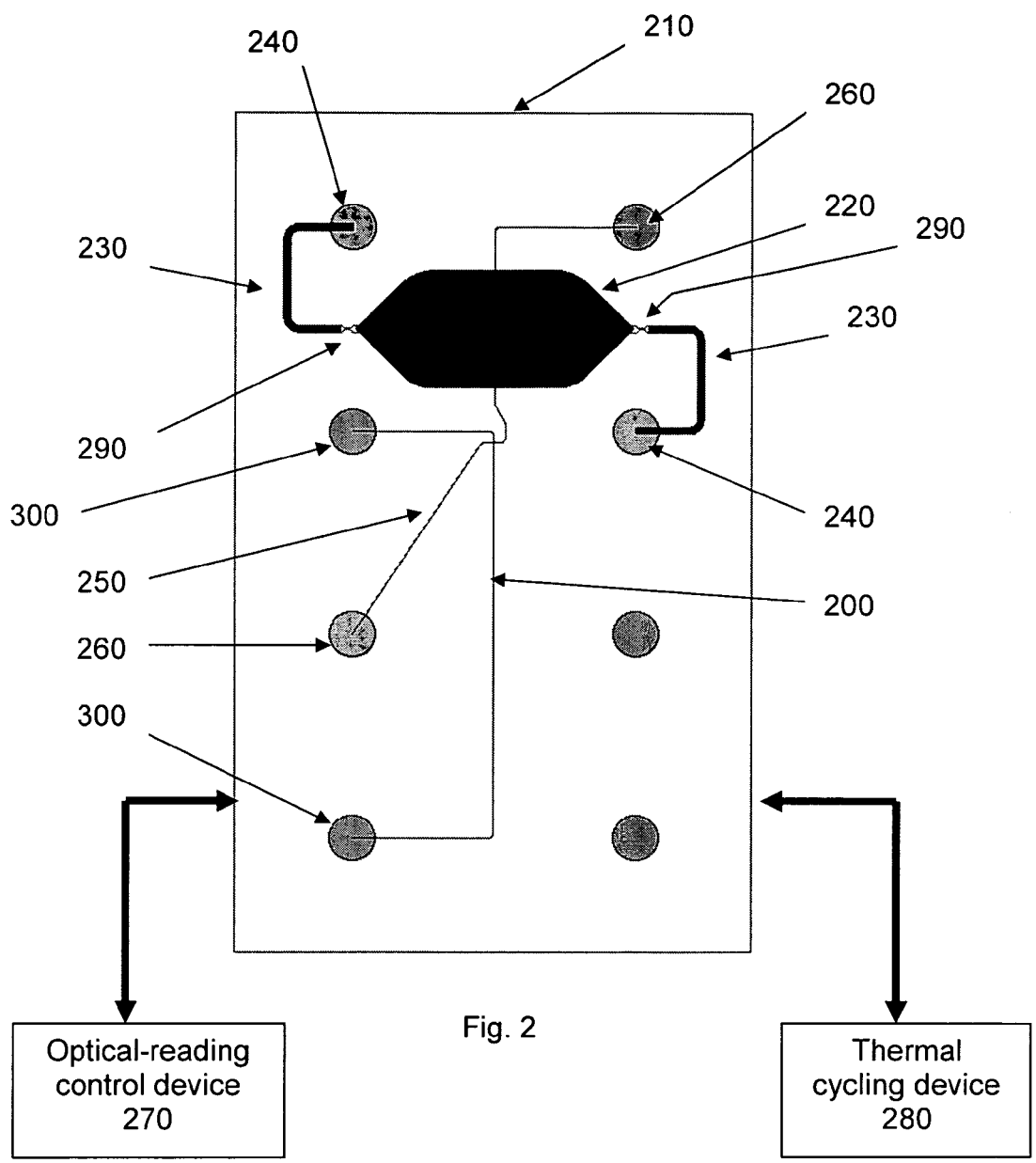
FIG. 2 is an embodiment of a microfluidic system of the present invention.
Figure 3:
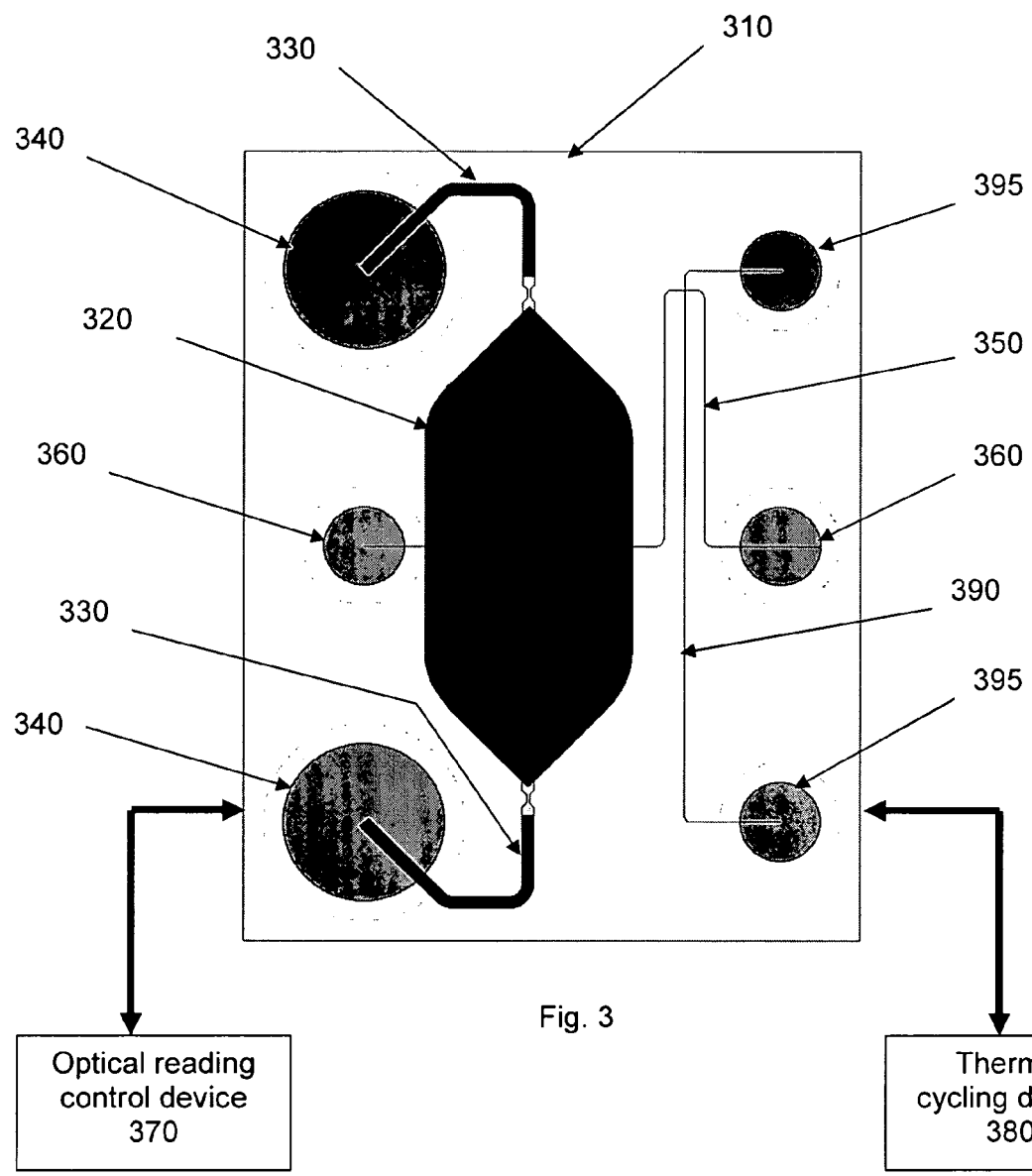
FIG. 3 is another embodiment of a microfluidic system of the present invention.

In a separation channel, the flow resistance equation is similarly presented as:

$$\Delta P = R_{sep} Q_{sep}$$

where $R_{sep}$ is the hydrodynamic flow resistance of the separation channel and $Q_{sep}$ is the flow rate through this channel. This equation is a simplification of most systems such as shown in FIG. 2 or FIG. 3, because in general there are multiple separation channels connected to the PCR chamber. The simplification is made here as an example to arrive at an order magnitude range of hydrodynamic resistance ratio. The hydrodynamic resistance $R_{sep}$ and the flow rate $Q_{sep}$ may be calculated more accurately by taking in account the actual channel topology of the system, which can, for example, be calculated as series and parallel connections of individual channel sections, but for the purposes of the calculation, the simple system is assumed to approximate the more complex situation.

A maximum flow rate of the separation channels can be defined by a certain allowable displacement of the solution. This maximum displacement $\Delta x$ can be defined in terms of the width of bands of a species being separated. The pressure-induced flow will cause dispersion of these bands. To avoid significantly adding to the dispersion of the separation, $\Delta x$ may set to be less than the width of the bands by a factor of at least two, or more. In a typical microfluidic DNA separation needed to analyze a PCR product, the bands are in the order of 100 micrometers wide, depending on the channel width. Therefore, $\Delta x$ is estimated to be between 10 and 50 micrometers.

If the cross-sectional area of the channels is A, the maximal allowable flow rate $Q_{sep}^{Max}$ can be written as:

$$Q_{sep}^{Max} = \frac{\Delta x A}{t_{anal}}$$

The minimum flow resistance $R_{sep}^{Min}$ in the channel (minimum separation channel resistance) required to ensure that the flow is below this value can be given by:

$$R_{sep}^{Min} = \frac{\Delta P t_{anal}}{\Delta x A}$$

The pressure difference and the analysis time are not known or fixed in general. So it is useful to express the requirement of a minimum separation channel resistance in terms of the ratio of separation channel resistance to PCR chamber resistance:

$$\left[\frac{R_{sep}}{R_{chamber}}\right]^{Min} = \frac{fV_{chamber}}{\Delta x A}$$

This expression therefore defines the minimum required ratio of flow resistance that will enable a valveless coupling of a PCR chamber and a set of channels for CE separation.

An estimated range of flow resistance ratio can be given based on this equation. For high-sensitivity PCR, a relatively high volume is required. For example, for detecting a pathogen at a concentration of 100 CFU/ml, a volume of at least several tens of microliters would be needed to ensure that at least one pathogen is present. An exemplary chamber volume is 25 µl. A fraction that can be lost without substantially affecting the assay can be assumed to be about 0.1; this fraction is an example and in some circumstances a greater fractional loss may be tolerated, although lower the better. Thus, an exemplary value of the nominator in the expression above is estimated to be 2.5 µl. The cross-section of the microfluidic channel may vary over a wide range, but in the microfluidic field, it has varied from, for example, about 10 µm to about 100 µm from side to side; and therefore for the present example, an average dimension of 30 µm by 30 µm is chosen. The range of values of $\Delta x$ as discussed above is chosen to be an average of 30 µm. The resulting value of the volume in the denominator is $2.7 \times 10^{-5}$ µl, and the ratio is then approximately given by:

$$\left[\frac{R_{sep}}{R_{chamber}}\right]^{Min} = 10^5$$

Clearly, this value depends on various assumptions, most notably the assumed value of the separation channel cross section. If the cross-sectional dimension is allowed to range from 10 µm to 100 µm from side to side, the following range for the resistance ratio is obtained:

$$\left[\frac{R_{sep}}{R_{chamber}}\right]^{Min} = 10^4 \text{ to } 10^6$$

In addition the other parameters have possible ranges, such as f could be between 0.02 and 0.2, and $V_{chamber}$ could range from 10 to 100 µl. If these further sources of variations are accounted for, the possible range extends to:

$$\left[\frac{R_{sep}}{R_{chamber}}\right]^{Min} = 10^3 \text{ to } 10^7$$

The above range is an example based on a number of assumptions as described above. The upper range or the lower range may be further increased or deceased depending on how the various parameters are defined. For example, the various parameters can be further adjusted to increase the upper range to about $10^9$.

A criterion for designing a microfluidic system may also be based on a ratio of volumes rather than a ratio of flow resistances. For example, assume both the separation channel and the large volume chamber (the volume of the flow channels is assumed to be included in the chamber volume to simplify the calculation) have a cross-sectional aspect ratio not too different from one for the purposes of calculation. This assumption may not be entirely accurate for a large volume chamber where, for example, the width to depth ratio can be 10 to 1, but to obtain an order of magnitude calculation of the volume ratio, this assumption would still be valid (for example, the correction factor for the 10:1 ratio above would only be about a factor of four). The flow resistance is represented as follows:

$$R = \alpha \frac{\mu L}{D^4}$$

where L is a length, µ is the dynamic viscosity, and D represents a cross-sectional dimension (e.g. a diameter). For a circular channel the numeric factor α equals to 128/π. Thus, the ratio of flow resistances can be re-written as follows:

$$\frac{R_{sep}}{R_{chamber}} = \frac{\mu_{sep}}{\mu_{chamber}} \frac{L_{sep}}{L_{chamber}} \left(\frac{D_{chamber}}{D_{sep}}\right)^4$$

Similarly, the ratio of volumes can be written as:

$$\frac{V_{chamber}}{V_{sep}} = \frac{L_{chamber}}{L_{sep}} \left(\frac{D_{chamber}}{D_{sep}}\right)^2$$

Thus the two ratios are related as follows:

$$\frac{V_{chamber}}{V_{sep}} = \left(\frac{\mu_{chamber}}{\mu_{sep}}\right)^{1/2} \left(\frac{L_{chamber}}{L_{sep}}\right)^{3/2} \left(\frac{R_{sep}}{R_{chamber}}\right)^{1/2}$$

Furthermore, for calculating the order of magnitude, the length ratio and the viscosity ratio are both assumed to be approximately equal to one. Then the volume ratio becomes equal to the square root of the resistance ratio, and for a range of $10^4$ to $10^6$ in the resistance ratio, the volume ratio range is:

$$\frac{V_{chamber}}{V_{sep}} = 10^2 \text{ to } 10^3$$

Thus, the total combined volume of the separation channels in the device may be 100 to 1000 less than the total combined volume of the PCR chamber and the flow channels, in order to allow CE analysis of samples from the PCR chamber without interaction between the CE and the PCR.

The viscosity in the separation channels may be higher, and the length of these channels may be longer. In those cases, the volume ratio can be appropriately calculated downward by an appropriate amount.

Fabricating such a system requires making channels with widely different dimensions. The dimensions of a PCR chamber are tied to its desired volume, which may vary according to the application. The chamber volume may be configured from about 1 µl to about 100 µl, about 10 µl to about 75 µl, or about 10 µl to about 50 µl, or about 10 µl to about 25 µl. Thus, for example, for a 25 µl volume chamber, the chamber dimension can be 10 mm by 5 mm by 500 µm. A depth of at least about 500 µm may be desirable to avoid the other dimensions from becoming excessively large. However, the dimension of the chamber is not limited to the above and may be appropriately varied and configured to achieve the desired volume.

The dimensions of the channels used for electrophoretic separation and detection can be much smaller; for example, they may have a cross section of 20 µm by 20 µm. The depth of the network of channels may be reduced down to 5 to 7 microns to increase the ratio of flow resistances. The dimensions above are merely examples and are not limited to those. As long as the dimensions between the PCR chamber and the network of channels can be made different enough to ensure that the ratio of hydrodynamic flow resistance in these channels to the resistance present in the PCR chamber and its access or flow channels is about $10^3$ or more, or about $10^3$ to about $10^9$, or about $10^3$ to about $10^7$, or about $10^4$ to about $10^6$, the actual dimensions can be appropriately varied. That is, the dimensions of the flow channels can be appropriately configured in relation to the PCR chamber to achieve the desired hydrodynamic flow resistance.

A polymer, for example, polymethyl methacrylate or cyclic olefin polymer, would be well suited to fabricate microfluidic structures of unequal dimensions in the same substrate and to make the resultant substrate disposable. A polymeric microfluidic device having unequal channel dimensions can be fabricated by the following method as shown in FIGS. 1(A) to 1(E). As shown in FIG. 1(A), select a double-sided polished silicon wafer 110 with a thickness equal to the desired deep channel, for example, in the range 500 to 600 µm. Then, photolithographically pattern the silicon on one side with the pattern for the shallow channels. The patterning can be a combination of photoresist, silicon oxide, and/or silicon nitride as masking layers for the next step. Then, etch shallow channels 120 with a high-aspect ratio plasma etch, such as deep reactive ion etching (DRIE) (FIG. 1(A)). Other etching techniques are also possible, but DRIE can be used to create deep, steep-sided holes and trenches in wafers. Turn the wafer 110 over, and photolithographically pattern the silicon on the other side with the pattern for deep channels 130, in alignment with the etched pattern on the other side. This requires some alignment method, such as using infrared light to look through the silicon wafers 110. Etch all the way through the silicon wafer with a high-aspect ratio plasma etch, such as DRIE (FIG. 1(B)). This creates an opening in the silicon wafer 110 at the location of the deep channels 130. Then, anodically bond the silicon wafer 110 to an unpatterned borosilicate glass wafer 140 (FIG. 1(C)). Then, make a Nickel inverse replica 150 of the silicon/glass wafer by electroplating (FIG. 1(D)). This replica 150 is called an electroform 150. Use the electroform 150 to compression mold or emboss a polymer substrate 160 (FIG. 1(E)). The polymer substrate 160 is then drilled at appropriate locations to make wells and the edges are cut to make a microfluidic chip, which can be laminated or pressure/temperature bonded with other materials. One method for sealing the channels is lamination with a thin polymer film.

Alternatively, the large volume features in the polymeric microfluidic chip such as the PCR chamber 220 can be fabricated by other methods such as CNC machining after the shallow separation channels have been fabricated by molding or embossing. This method is slower, since it must be repeated for every device, but has the advantage of allowing more flexibility in the design of the large volume feature.

Deep etching is carried out on the wafer 110 for making a part of the electroform 150 that will produce a PCR chamber with a volume of, for example, about 25 µl. FIG. 2 shows an embodiment of a microfluidic system. A polymer chip 210 can be made with a PCR chamber 220 having a depth of 500 µm and an area of 50 mm$^2$, or a square of 7×7 mm. Other dimensions are also possible and the depth, width, and height can be appropriately controlled in accordance with the desired volume of the chamber. In addition, the chamber has access or flow channels 230 that connect the chamber to flow wells 240 to allow the chamber to be filled with appropriate solutions.

The PCR chamber 220 is also connected directly or indirectly to separation channels, which are separate from the flow wells 240. The separation channels are general term used to include, among others, a loading channel 250 that can be used to introduce a faction of the amplified DNA and a CE channel 200 which intersects (intersecting area) with the loading channel 250 and can be used to execute electrophoretic separation to detect the size of the amplified DNA. Only one loading channel 250 and one CE channel 200 are shown in FIG. 2 but the chip may be configured to have more than one each. An internal volume of the separation channels (e.g. the loading channel 250 and the CE channel 200) can be designed to be 100 times or more smaller or from about 100 times to about 1000 times smaller or from about 300 times to about 1000 times smaller than the combined volumes of the PCR chamber 220 and the flow channels 230. The dimensions of the PCR chamber 220 and its flow channels 230 and the dimensions of the loading channel 250 and the CE channel 200 can be so varied to provide a ratio of hydrodynamic flow resistance in these channels to the hydrodynamic flow resistance present in the PCR chamber 220 and its flow channels 230 to be about $10^3$ or more, or about $10^3$ to about $10^9$, or about $10^3$ to about $10^7$, or about $10^4$ to about $10^6$. By having the hydrodynamic resistance the loading channel 250 and the CE channel 200 made high in comparison to the PCR chamber 220, a gate function for the channels can be achieved without having a valve or a plug. The polymer chip 210 is also provided with an optical-reading control device 270 for reading and processing signals from the polymer chip 210 and a thermal cycling device 280 for thermally cycling the PCR chamber 220.

The loading channel 250 is connected to loading wells 260 at the opposite ends not connected to the PCR chamber 220. The loading wells 260 can function as an electrical contact for introduction and/or injecting the DNA. The opposite ends of the CE channel 200 are connected to respective CE wells 300. The CE wells 300 can function as an electrical contact for electrophoresis. This arrangement avoids placing electrodes in the two flow wells 240 connected to the PCR chamber 220 by the flow channels 230. The flow wells 240 need to have large enough combined volume to fill the chamber 220. In the design above, the loading wells 260 are kept separate from the flow wells 240 and are connected to a power supply to provide voltage to the electrodes. The CE wells 300 are also kept separate from the flow wells 240 and are connected to a power supply to provide voltage to the electrodes. This arrangement facilitates sealing the flow wells during temperature cycling. Furthermore, a flow resistor 290 can be optionally provided at each end of the PCR chamber to avoid excessive flow between the chamber and the wells during cycling.

FIG. 3 shows another embodiment of a microfluidic system. A polymer chip 310 has a PCR chamber 320, which is connected to flow channels 330 that lead to flow wells 340. In addition to the flow channels 330, the PCR chamber 320 is connected directly or indirectly to separation channels. The separation channels include a loading channel 350, whose ends lead to loading wells 360, and a CE channel 390, which intersects (intersecting area) the loading channel 350 and whose ends respectively lead to CE wells 395. Only one loading channel 350 and one CE channel 390 are shown in FIG. 3 but the chip may be configured to have more than one each. This design is much more compact than the previous embodiment and thus would be more economical to fabricate because more chips can be made from a single electroform. The limiting factor may be the need to separate the separation channels (i.e. the loading channel 350 and the CE channel 390) from the PCR chamber 320 sufficiently to ensure that the temperature cycling for the PCR does not perturb the separations. As with the previous embodiment, the combined volume of the separation channels (the loading channel 350 and the CE channel 390) can be 100 times or more smaller or from about 100 times to about 1000 times smaller or from about 300 times to about 1000 times smaller than the combined volume of the PCR chamber 320 and the flow channels 330. The dimensions of the PCR chamber 320 and its flow channels 330 and the dimensions of the loading channel 350 and the CE channel 390 can be so varied to provide a ratio of hydrodynamic flow resistance in these channels to the hydrodynamic flow resistance present in the PCR chamber 320 and its flow channels 330 to be about $10^3$ or more or about $10^3$ to about $10^9$, or about $10^3$ to about $10^7$, or about $10^4$ to about $10^6$. By having the hydrodynamic resistance of the loading channel 350 and the CE channel 390 made high in comparison to the PCR chamber 320, a gate function for the channels can be achieved without having a valve or a plug. The polymer chip 310 is also provided with an optical-reading control device 370 for reading and processing signals from the polymer chip 310 and a thermal cycling device 380 for thermally cycling the PCR chamber 320.

Figure 4:
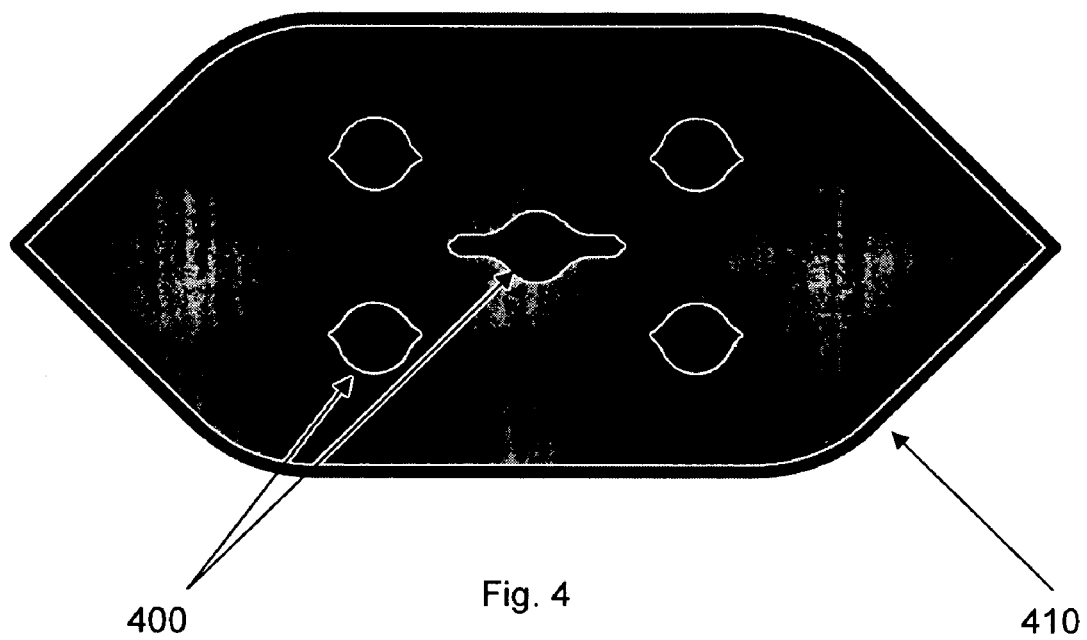
FIG. 4 is another embodiment of a microfluidic device of the present invention.

Other possible features of the PCR chamber are some internal support structures to avoid having the laminate film sag when it has a relatively large area to cover. For example, as shown in FIG. 4, an embodiment showing internal support structures 400 are placed within a PCR chamber 410 to support the laminated film from sagging. The support structures 410 here are four structures at rectangular corners within the chamber 410 and a fifth support structure at the center, where the PCR chamber has a width of 5.4 mm at its widest, a depth of 0.5 mm, and a total volume of 25 µl. The dimensions provided here are examples and do not limit the chamber. The structures 410 are connected at the bottom of the chamber and at the laminated film placed over the chamber 410. The size, the number, and the layout of the support structures may be appropriately configured in respect to the size and the volume of the chamber to insure that no sagging of the laminated film occurs. That is, the support structures may be one or more and may be laid out in view of the volume, the depth, and the width of the chamber to best support the laminated film. The material of the support structures may be made of the same polymeric material as the PCR chamber but it could also be different so long as it is inert and does not react with any solution disposed in the chamber.

The devices described in the embodiments shown above are designed for executing real-time PCR-CE in that, in the course of an amplification, several samples of DNA can be taken and analyzed by the CE component integrated in the polymer chip. The fraction of the DNA removed is so small that it has no significant impact on the PCR process. If electro-osmotic flow in the separation channels is suppressed, as is usually the case in DNA separations, then the DNA is moved entirely by electrophoresis, and no volume is removed from the PCR chamber. A sample can be taken and analyzed for each PCR cycle, or every other PCR cycle. This is possible because PCR cycles in microfluidic chips generally take 15 sec to 60 sec, and the fastest microfluidic DNA separations are in the order of 60 sec or faster. In addition, the time interval between taking samples could be shorter than the time required for separation, because it is possible to separate multiple samples simultaneously. The fact that multiple points can be sampled means that a single point can also be sampled at the end of the amplification (end-point PCR-CE).

The method involved in using the devices for microchip PCR with real-time CE detection such as those described in the embodiments can be executed as follows: The method refers to the exemplary systems shown in FIG. 2 and FIG. 3. Fill the shallow electrophoretic, CE channels 200 or 390 of a microchip 210 or 310 with a DNA sieving matrix. This matrix can also be coated on the channel walls sufficiently to suppress electro-osmotic flow, and can have a fairly high viscosity, for example, about 10 to 20 centipoise, to help reduce any pressure-induced flows, and increase the ratio of hydrodynamic flow resistance between the channels and the PCR chamber. The matrix can also contain an appropriate intercalating dye such as ethidium bromide, Cyber Green, Evergreen, or Syto dyes, for detecting the DNA fragments. Then, fill the PCR chamber 220 or 320 with a mixture containing the sample, and all PCR reagents, including any required enzyme. Further, seal the PCR flow wells 240 or 340, and place the chip in a temperature cycling system. Then, while the amplification by the temperature cycling is taking place, during the amplification (each cycle, or every other cycle), apply a voltage on the electrophoretic, loading wells 260 in the case of FIG. 2 or wells 360 in the case of FIG. 3 to introduce a fraction of the DNA from the PCR chamber into the loading channels 250 or 350. Then, by applying a voltage on the CE wells 300 or 395, the part of this DNA is injected into the CE channels 200 or 390 through the intersecting area. Further, separate the DNA, and detect it at a suitable distance from the intersecting area. The separation field and separation length can be optimized for rapid separation of relatively small double-stranded DNA fragments. Then, in each separation, identify the peak corresponding to the desired PCR amplicon, and calculate its size by the height or the area. Then, plot the obtained peak sizes as a function of cycle number, and use these data to determine the original amount of target DNA present in the sample.

A typical single PCR cycle includes three steps: denaturation, primer binding or annealing, and DNA synthesis or extending. During denaturation, the starting mixture is first heated to about 94° C. to 96° C. for separating the double strands DNA template. After denaturation of the DNA, the mixture is cooled to about 55° C. to allow the primers to bind to their complementary sequences on the separated strands. The primers define the ends of the DNA to be duplicated. Then the mixture is heated to a temperature for about 72° C., so that the DNA polymerase catalyzes the extension of the annealed primers on the template strands, and this one cycle is repeated one or more times.

In some cases, a single PCR cycle includes only two steps: denaturation, and primer binding combined with DNA synthesis. In this case, the starting mixture is first heated to about 94° C. to 96° C. for separating the double strands DNA template. After denaturation, the mixture is cooled to a defined temperature (about 60 to 70° C.) to allow the primers to bind to their complementary sequences on the separated strands and to allow the DNA polymerase to catalyze the extension of the annealed primers on the template strands, and this one cycle is repeated one or more times.

It is possible to perform PCR amplification at lower temperatures. For example, an additive or additives such as proline are included in the reaction mixture to decrease the template DNA denaturation temperature. For sample, a low temperature cycle PCR can be carried by a low denaturation temperature about 75° C. and primer annealing and extending temperatures at about 55° C.

In another example, DNA can be amplified without the need for thermocycling. For example, the DNA template is separated by an enzyme called helicase instead of by heat. Thus DNA can be amplified at a single temperature without the use of thermocycling.

A part of a reaction sample, for example, PCR amplicon, reacted in the chamber is injected into the separation channel by applying appropriate voltages, not after finishing the amplification by PCR temperature cycling but during the amplification by PCR temperature cycling. The PCR amplicon injected into separation channel is separated at the separation channel. Then, the separated PCR amplicon is detected. Further, these injection step, separation step and detection step are repeated one or more times.

The determination of the original amount of target nucleic acid present in the sample can be conducted by collecting the data obtained by repeating the detection process and by quantifying the amount of nucleic acid present based on the data collected. For example, the quantification of the amount of nucleic acid present can be determined by calculating a threshold cycle.

As an example, PCR-CE experiments with the PCR chip 210 in FIG. 2 will now be described. The reagents used in the experiments were: BSA solution (100 µg/ml); BCG genomic DNA, $10^6$ copies/µl; rTaq DNA polymerase, 5 U/µl; 10×PCR buffer; 50 mM $MgCl_2$; 10 mM dNTP; IS_F10 forward primer, CTCACCTATGTGTCGACCTG, 5 µM; and IS_R8 reverse primer, GGTCGAGTACGCCTTCTTG, 5 µM. A PCR reaction solution (28 µl) contained: 1×PCR buffer; 0.4 mM dNTP; 3 mM $MgCl_2$; 250 nM Forward primer; 250 nM Reverse primer; 1 µl BCG genomic DNA ($10^5$ copies); and 1 U rTaq DNA Polymerase.

The CE channels 200 of the PCR-CE chip 210 were filled with a polydimethylacrylamide gel matrix containing an intercalating dye, and 28 ul of a PCR reaction mix was loaded on to the PCR chip 210 from one well 240. The PCR reagents and gel filled PCR chip was then clamped with the thermal cycling device of a thermal cycler 280. A pressure of 30 psi was applied to all the wells through a manifold device placed over and hermetically covering the chip 210 to suppress evaporation during the PCR cycling. The manifold device is described in more detail in PCT/US2008/06266 filed on May 15, 2008, which claims the benefit of U.S. provisional application No. 60/938,171, filed on May 15, 2007, both of which are hereby incorporated by reference in their entirety. PCR was performed using the following cycle protocol: 1×96° C., 30 s; and 40×96° C., 15 s, 62° C., 15 s, and 72° C., 30 s.

Figure 5:
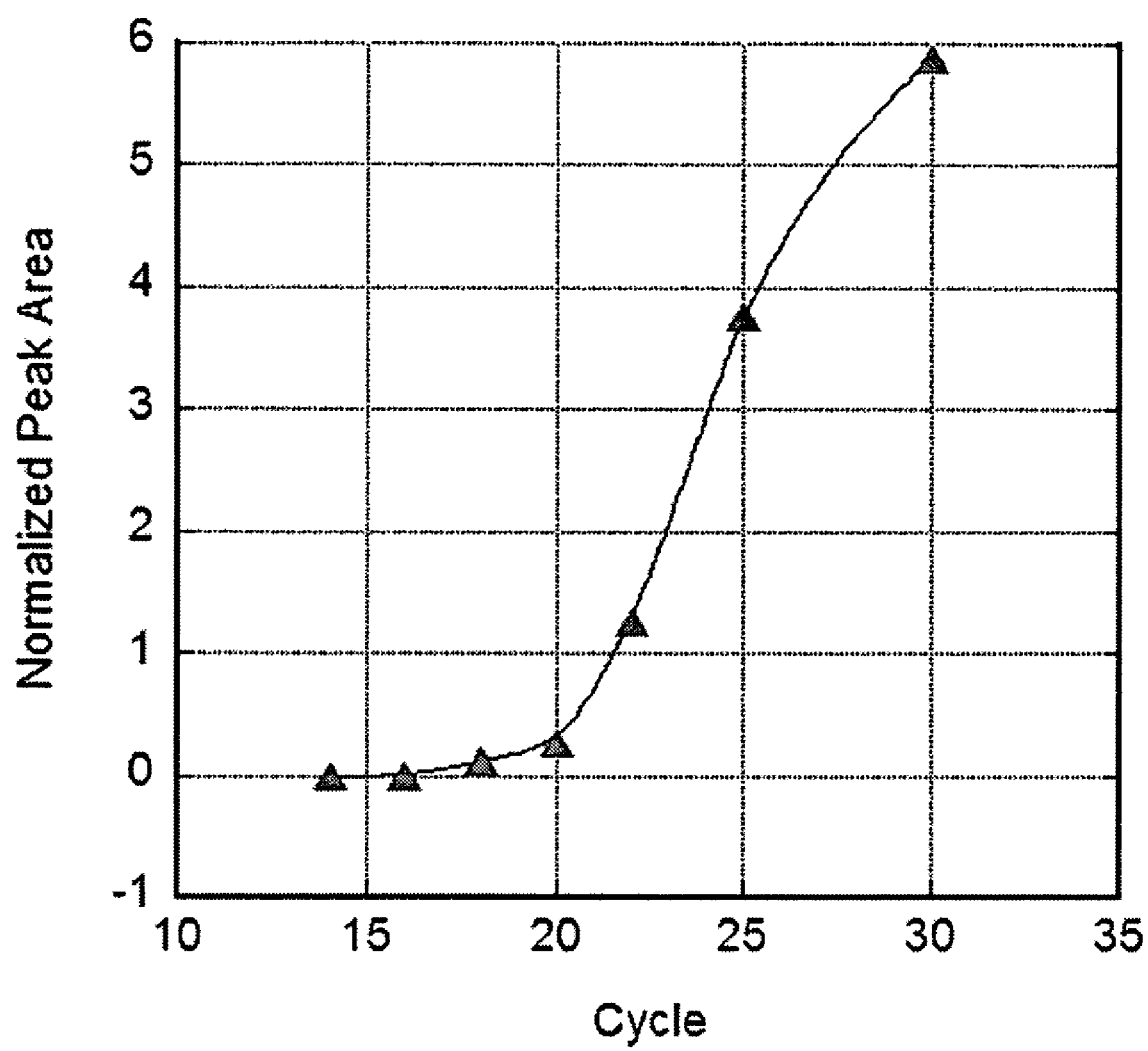
FIG. 5 shows an exemplary real-time PCR growth curve generated by using an embodiment of a microfluidic device of the present invention.
Figure 6:
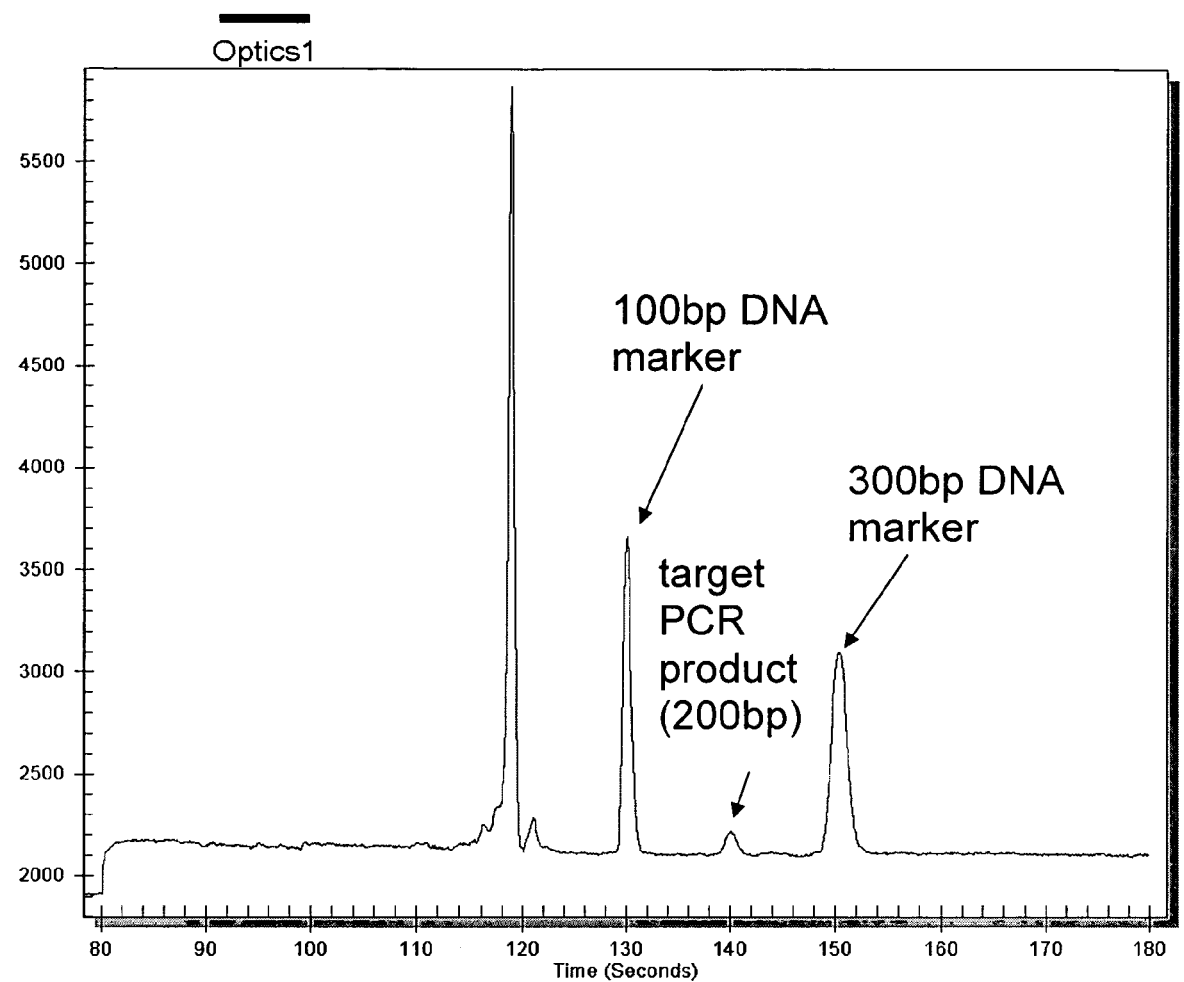
FIG. 6 shows an exemplary CE separation graph of an embodiment of a microfluidic device of the present invention.

By applying a voltage between the loading wells 260 at cycles 14, 16, 18, 20, 22, 25, and 30, PCR product samples from the chamber 220 were induced to migrate into the loading channel 250. Then, by applying a voltage between the CE wells 300, PCR product samples were injected into CE channel 200 to separate and were analyzed by the optical reading control device 270. The peak area of the PCR product was normalized using an internal marker (100 bp DNA) in the PCR mix and plotted against the cycle number to generate the PCR growth curve, as shown in FIG. 5. FIG. 6 shows an electropherogram of CE separation at the $18^{th}$ cycle when the target PCR product sample (200 bp) starts to be detectable. The total time was 1 hour.

required reagents for the PCR reaction (primers, enzyme, buffers, magnesium chloride, dNTP's), and different copy numbers of the target. The target was 200 bp fragment of plasmid DNA. The channel 605 connected between the chamber 610 and a loading electrode well 5 was filled with PCR buffer. After all channels and chambers were filled, each well was filled with separation gel or markers or PCR buffer.

The chip 600 was then placed on a thermal cycling device (not shown) consisting of a flat copper plate connected to a heater and a cooling means. A pressure of 37 psi was applied through a manifold device (described in PCT/US2008/06266) to all the wells at once. The thermal cycling was set to 40 cycles, with the following timing: denaturing 15 s, annealing 20 s, and extension 15 s. The total cycling time was 2100 s. After the PCR cycles, the pressure was released slowly.

After the thermal cycling, on-chip capillary electrophoresis was performed. Voltages were applied in the wells using inserted platinum electrodes, while optical detection was carried out with a fluorescent microscope. The incident light came from a green diode laser at 532 nm, and the excitation filter was at 610±35 nm.

The sample from the PCR chamber was electrophoretically moved toward the well 8, while being mixed with DNA size markers (100 bp and 700 bp) from the well 3. At the same time, currents from the wells 1 and 7 were also directed to the intersection to confine the sample at that intersection. In the next step, the DNA was directed from a well 7 to a well 1 to perform the separation, while a pull-back current is maintained in the sample loading channels from wells 8 and 3. The following table shows the applied voltages and currents for the CE separation:

| step | time (s) | 1 | 2 | 3 | 4 | 5 | 6 | 7 | 8 |
|---|---|---|---|---|---|---|---|---|---|
| loading | 140 | −3 uA | 0 uA | −15 uA | 0 uA | −30 uA | 0 uA | −3 uA | 2100 V |
| separation | 45 | 1900 V | 0 uA | 3 uA | 0 uA | 0 uA | 0 uA | 800 V | 3 uA |

There are various methods known for calculating relative quantification in real-time PCR. For example, U.S. Pat. No. 6,942,971, in order to quantify the amount of DNA, describes a program to store signal values defining a growth curve for the nucleic acid sequence, determine a derivative of the growth curve, and calculate a cycle number or time value associated with a characteristic of the derivative. In Yuan et al. BMC Bioinformatics 7:85 (2006), the authors provide a statistical analysis of real-time PCR data to quantify the amount of DNA produced. In Pfaffl, Nucleic Acid Research, vol. 29, No. 9 (2001), the author describes a new mathematical model for relative quantification in real-time PCR. Any these methods and others known in the art could be used to quantify the amount of nucleic acid in real time PCR.

Figure 7:
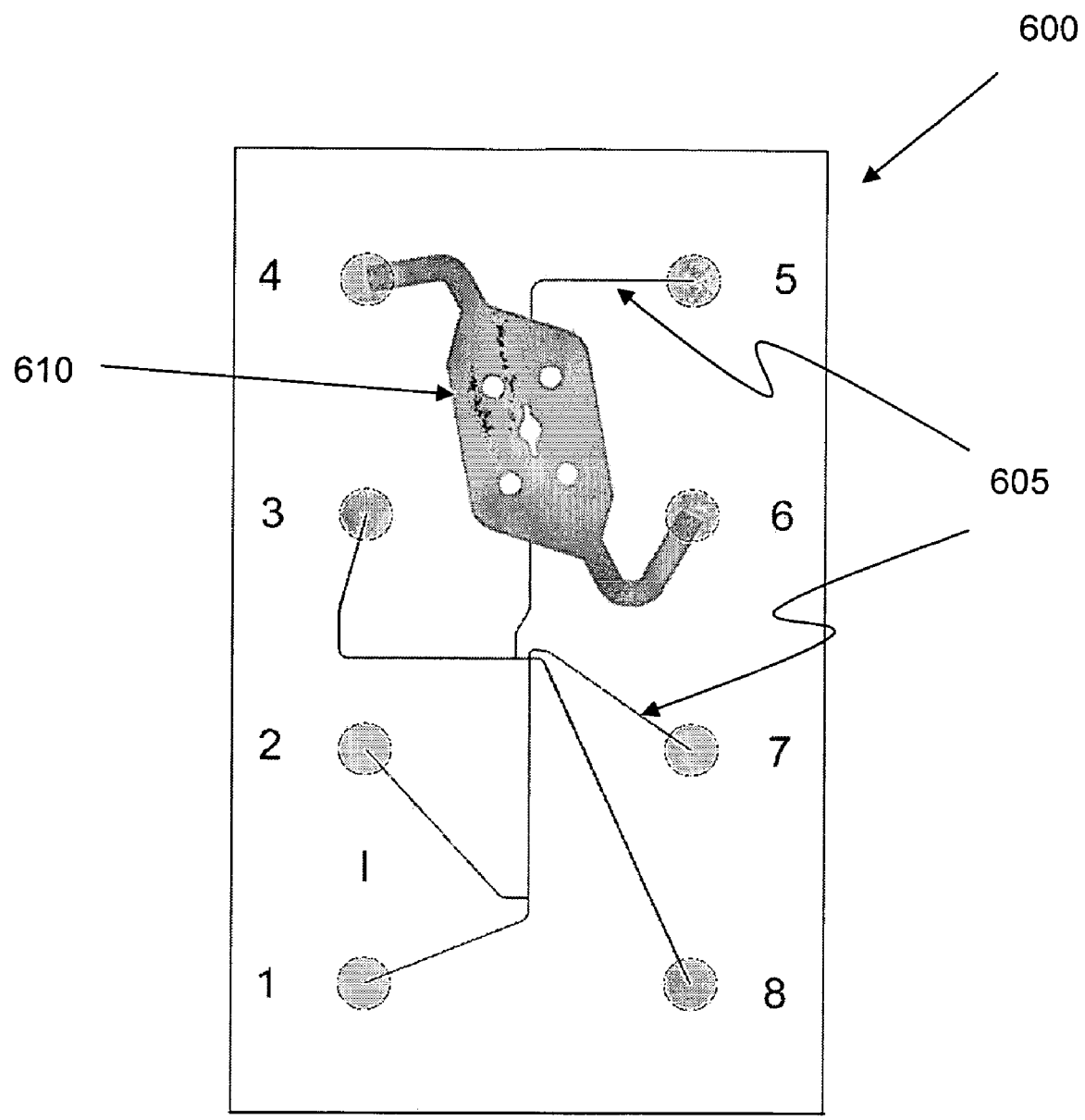
FIG. 7 illustrates another embodiment of a microfluidic device of the present invention.
Figure 8:
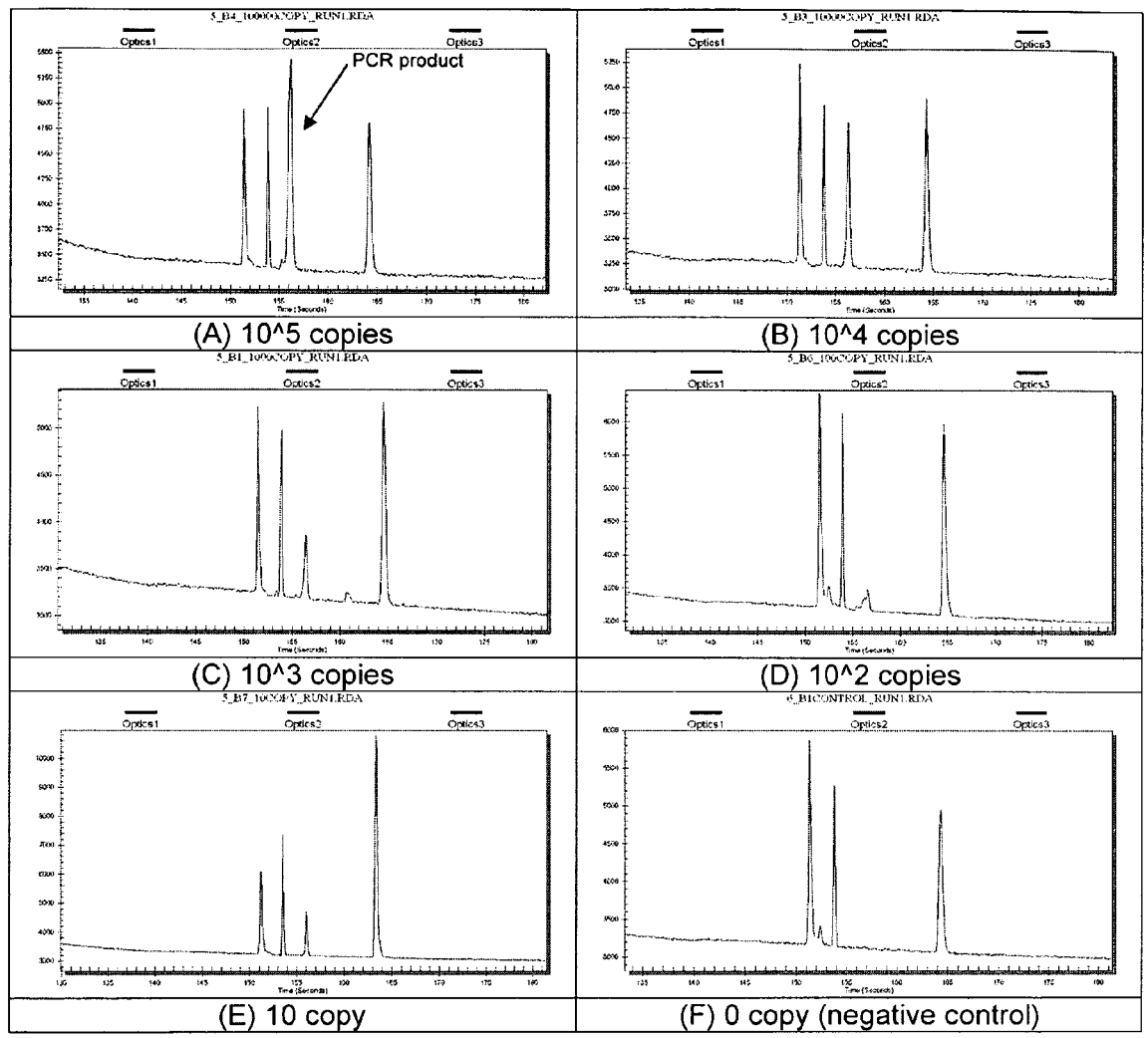
FIGS. 8(A)-(F) show results of an end-point PCR assay using an embodiment of a microfluidic device of the present invention.

In another embodiment, an end-point PCR assay is demonstrated. A microfluidic chip 600 for PCR with CE detection, as shown in FIG. 7, has channels 605 each of about 30 µm in width and a PCR chamber 610 of about 500 µm in depth. Basically, the dimensions of the chip 600 with wells 1-8 are the same as the one shown in FIG. 2.

Figure 9:
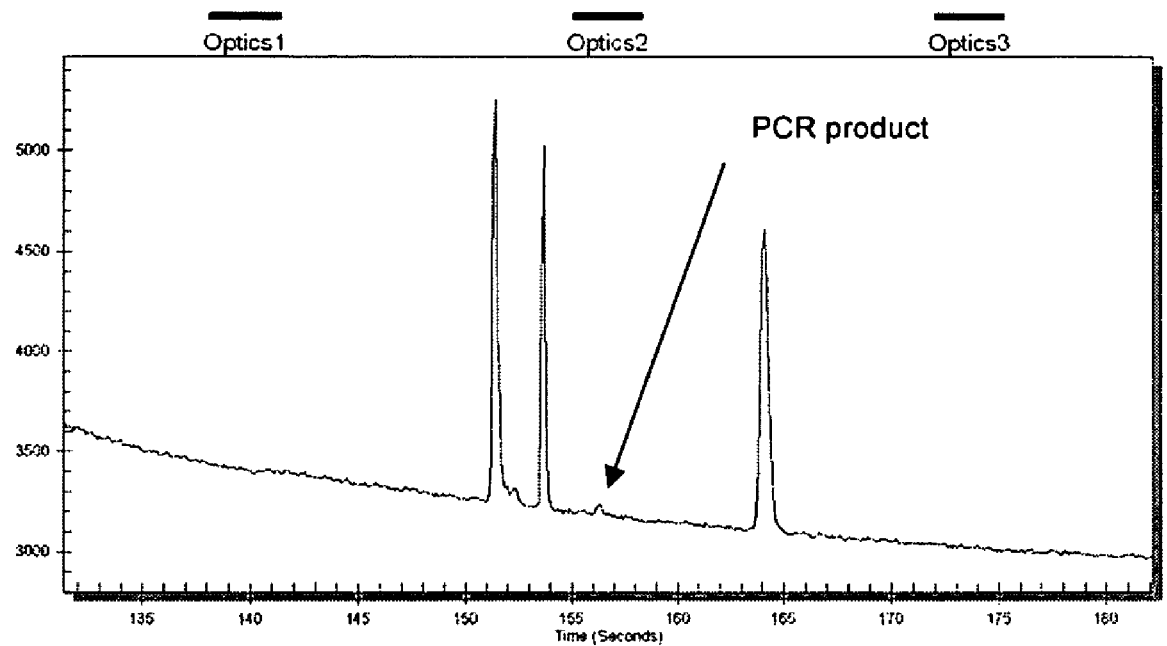
FIG. 9 shows another result of an end-point PCR assay using an embodiment of a microfluidic device of the present invention.

To conduct the end-point PCR assay, the channels were first filled with separation gel, which consists of 200 mM TAPS buffer at pH 8, 2% polydimethylacrylamide sieving matrix, and ethidium bromide dimer fluorescent dye. Then the chamber 610 was loaded with PCR buffers containing all FIGS. 8(A)-(F) show the CE results for a series of experiments performed as described above, with different original copy numbers of the target DNA in the PCR buffer—$10^5$, $10^4$, $10^3$, $10^2$, 10, and zero (control) copy number. The results show that the product resulting from the amplification of 10 original copies amplification is still detectable. As shown in FIG. 9, this experiment with 10 copies ('10_day2' in the table) was repeated on a subsequent day. The amplified peak is still detectable although it is much smaller.

The amplitude of each peak in this experiment can be used to estimate the DNA concentration, based on a separately performed calibration experiment. The result of the determination of concentrations from the present exemplary microfluidic device and on from other devices are presented in the table below.

After the PCR runs shown in FIGS. 8(A)-(F) and FIG. 9, samples were taken out of the chips and analyzed on a Agilent 2100 Bioanalyzer, which can be used to determine the concentration of each peak. Another control experiment was performed on the same PCR on Cepheid's SmartCycler®, which also reports a DNA concentration. The combined results are shown in the following table:

TABLE

Comparison of the PCR products using different devices and detections

| Sample (original copy numbers) | Microchip result: peak area ratio of target and 100 bp (marker) | Microchip result: Target concentration from calibration (ng/μL) | Microchip PCR: sample analyzed on Bioanalyzer (ng/μL) | Control PCR reaction on SmartCycler (ng/μL) |
|---|---|---|---|---|
| 100000 | 3.06 | 13.87 | 21.5 | 26.5 |
| 10000 | 1.43 | 6.48 | 11.3 | 14.5 |
| 1000 | 0.70 | 3.16 | 8.6 | 10.7 |
| 100 | 0.38 | 1.72 | 1.02 | 4.4 |
| 10 | 0.50 | 2.27 | 1.5 | 3 |
| 10_day 2 | 0.14 | 0.62 | 0.92 | |
| 0 | 0 | 0 | 0 | 0 |

It is shown that the microfluidic chip has comparable sensitivity, if not better, as the other detection devices. The variation of results can be explained by the statistical fluctuation of the number of copies actually present each time the dilution is performed. The quantitative levels of DNA present after each amplification were similar with all methods, and increased monotonically with the original copy number of the target.

There are many variations and added features possible that can be added to the designs and method described above. One example is an on-chip mixing of the sample and the PCR mixture by using an extra large-volume well. This example would involve using an external pipettor to place in a well in succession the sample to be analyzed and the PCR master mix that contains the primers, enzyme, and nucleotides. Such a well would require a volume at least as great as the PCR chamber, in the range of about 10 to about 100 microliter. Another example is an on-chip mixing of the DNA sample from the PCR reaction with a sizing standard. To do this requires adding an extra well, that contains the DNA standard or markers, and a channel that connects that well to the portion of the channel between the PCR chamber 220, and the injection intersection. The ratio of the mixing between the sample of DNA from the PCR chamber and the DNA standards can be controlled by the applied voltage or currents to the separation wells 260 and the additional DNA marker well.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A microfluidic system for nucleic acid amplification and detection, comprising:
    a substrate having a chamber for amplification of a volume of nucleic acid;
    a plurality of wells disposed on the substrate;
    flow channels connecting the wells and the chamber in the substrate to allow for flow of solution through the chamber; and
    one or more separation channels provided in the substrate, connecting the chamber and other wells for separating and detecting a fraction of the amplified nucleic acid in the chamber,
    wherein the chamber, the flow channels, and the one or more separation channels are configured such that the hydrodynamic flow resistance of the chambers and the flow channels combined is at least $10^3$ times smaller than the hydrodynamic flow resistance in the one or more separation channels.

2. The microfluidic system according to claim 1, further comprising a thermal cycling device for conducting amplification of nucleic acid in the chamber.

3. The microfluidic system according to claim 1, wherein a ratio of the hydrodynamic flow resistance in the one or more separation channels to the hydrodynamic flow resistance of the chambers and the flow channels is between about $10^3$ and about $10^9$.

4. The microfluidic system according to claim 1, further comprising an optical-reading control device for optically detecting signals from the nucleic acid fraction separated electrophoretically and for processing the signals.

5. A microfluidic system for nucleic acid amplification and detection, comprising:
    a substrate having a chamber for amplification of a volume of nucleic acid;
    wells disposed on the substrate;
    flow channels connecting the wells and the chamber in the substrate to allow for flow of solution through the chamber; and
    one or more separation channels provided in the substrate and connected to the chamber for separating and detecting a fraction of the amplified nucleic acid in the chamber,
    wherein the one or more separation channels have a combined volume that is at least 100 times smaller than the combined volume of the chamber and the flow channels.

6. The microfluidic system according to claim 5, further comprising a thermal cycling device for conducing amplification of nucleic acid in the chamber.

7. The microfluidic system according to claim 5, further comprising an optical-reading control device for optically detecting signals from the nucleic acid fraction separated electrophoretically and for processing the signal.

8. The microfluidic system according to claim 5, wherein the combined volume of the one or more separation channels is about 100 times to about 1000 times smaller than the combined volume of the chamber and the flow channels.

9. A microfluidic device for nucleic acid amplification and detection, comprising:
    a substrate having a chamber for amplification of a volume of nucleic acid;
    a plurality of wells provided in the substrate;
    flow channels connecting the wells and the chamber in the substrate to allow for flow of solution through the chamber; and
    one or more separation channels provided in the substrate, connecting the chamber and other wells for separating and detecting a fraction of the amplified nucleic acid in the chamber, wherein the chamber, the flow channels, and the one or more separation channels are configured such that the hydrodynamic flow resistance of the chambers and the flow channels combined is at least $10^3$ times smaller than the hydrodynamic flow resistance in the one or more separation channels.

10. The microfluidic device according to claim 9, wherein the chamber, the flow channels, and one or more separation channels are configured such that the hydrodynamic flow resistance of the chambers and the flow channels combined is about $10^3$ to about $10^9$ times smaller than the hydrodynamic flow resistance in the one or more separation channels.

11. The microfluidic device according to claim 9, wherein the chamber has a volume of about 10 µl to about 25 µl.

12. The microfluidic device according to claim 9, wherein a volume of the one or more separation channels is at least 100 times smaller than a combined volume of the chamber and the flow channels.

13. The microfluidic device according to claim 9, wherein a volume of the one or more separation channels is about 100 times to about 1000 times smaller than a combined volume of the chamber and the flow channels.

14. The microfluidic device according to claim 9, wherein more than one separation channels are provided in the substrate to form a network of channels for an electrophoretic DNA sizing assay.

15. A method for nucleic acid amplification and detection for a microfluidic device, comprising:
  (1) providing a microfluidic device containing a chamber for amplifying a volume of nucleic acid, wells, and flow channels connected to the wells and the chamber to allow for flow of solution through the chamber, and one or more separation channels connected to the chamber, wherein the chamber, the flow channels, and the one or more separation channels are configured such that the hydrodynamic flow resistance of the chambers and the flow channels combined is at least $10^3$ times smaller than the hydrodynamic flow resistance in the one or more separation channels;
  (2) disposing a solution of nucleic acid in the chamber;
  (3) amplifying the nucleic acid disposed in the chamber;
  (4) introducing a fraction of the amplified nucleic acid from the chamber into the one or more separation channels;
  (5) separating the fraction of the amplified nucleic acid through the one or more separation channels; and
  (6) detecting the separated nucleic acid,
  wherein steps (3) to (6) are repeated one or more times, or step (3) is repeated one or more times and then steps (4) to (6) are executed once.

16. The method according to claim 15, wherein the amplification of the nucleic acid disposed in the chamber is conducted by thermal cycling.

17. The method according to claim 15, further comprising (7) quantifying the amount of nucleic acid present based on data collected.

18. The method according to claim 15, wherein the quantification of the amount of nucleic acid present is determined by calculating a threshold cycle.

19. The method according to claim 15, wherein the chamber, the flow channels, and one or more separation channels are configured such that the hydrodynamic flow resistance of the chambers and the flow channels combined is about $10^3$ times to about $10^9$ times smaller than the hydrodynamic flow resistance in the one or more separation channels.

20. The method according to claim 15, wherein the chamber has a volume of about 10 µl to about 25 µl.

21. The method according to claim 15, wherein a volume of the one or more separation channels is at least 100 times smaller than a combined volume of the chamber and the flow channels.

22. The method according to claim 15, wherein a volume of the one or more separation channels is about 100 times to 1000 times smaller than a combined volume of the chamber and the flow channels.

23. The method according to claim 15, wherein more than one separation channels are provided in the substrate to form a network of channels for an electrophoretic DNA sizing assay.

* * * * *